(12) United States Patent
Orbay et al.

(10) Patent No.: US 6,273,892 B1
(45) Date of Patent: *Aug. 14, 2001

(54) FRACTURE FIXATION SYSTEM

(75) Inventors: Jorge L. Orbay; Javier Castañeda; Ernesto Hernandez, all of Miami, FL (US)

(73) Assignee: Hand Innovations, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/388,879

(22) Filed: Sep. 2, 1999

Related U.S. Application Data

(63) Continuation-in-part of application No. 09/150,792, filed on Sep. 10, 1998, now Pat. No. 6,200,321.

(51) Int. Cl.[7] .................................................. A61B 17/58
(52) U.S. Cl. ............................... 606/96; 606/86; 606/104
(58) Field of Search ...................... 606/53–75, 79–80, 606/99, 103–4, 184–185, 96, 86; 623/16, 22; 604/264, 164–170

(56) References Cited

U.S. PATENT DOCUMENTS

| | | | |
|---|---|---|---|
| 4,169,470 | * 10/1979 | Ender et al. | 606/62 |
| 4,381,770 | * 5/1983 | Neufeld | 128/92 |
| 4,541,423 | 9/1985 | Barber | 128/92 E |
| 4,790,304 | * 12/1988 | Rosenberg | 128/92 |
| 5,057,103 | * 10/1991 | Davis | 606/62 |
| 5,135,527 | * 8/1992 | Ender | 606/62 |
| 5,139,500 | 8/1992 | Schwartz | 606/96 |
| 5,171,277 | 12/1992 | Roger | 623/16 |
| 5,180,388 | * 1/1993 | Dicarlo | 623/16 |
| 5,281,225 | * 1/1994 | Vicenzi | 606/62 |
| 5,330,468 | 7/1994 | Burkhart | 606/96 |
| 5,391,171 | * 2/1995 | Schmieding | 606/104 |
| 5,488,761 | 2/1996 | Leone | 29/2.25 |
| 5,499,984 | 3/1996 | Steiner et al. | 606/80 |

(List continued on next page.)

FOREIGN PATENT DOCUMENTS

3924610 * 3/1990 (DE) .............................. A61B/17/58

* cited by examiner

*Primary Examiner*—Cary E. O'Connor
(74) *Attorney, Agent, or Firm*—David P. Gordon; David S. Jacobson; Thomas A. Gallagher

(57) ABSTRACT

A fracture fixation system is provided for the insertion of a fixation pin into the medullary canal of a fractured metacarpal, metatarsal, or phalangeal bone for stable bone fixation. The system includes one or more pins and an instrument for implanting the pins. According to one embodiment of the invention, the instrument includes a main handle and a pin handle movable relative to the main handle. The main handle includes a distal end, a drill coupled to the distal end, and a longitudinal slot which receives the pin handle. The drill includes a shaft having a distal boring tip and a groove proximal the boring tip for guiding the fixation pin. The pin handle is shaped and sized to slidably move within the longitudinal slot. Each pin preferably includes a curved, distal end. The distal end rests within the groove of the drill shaft. Movement of the pin handle within the slot of the main handle distally relative to the main handle causes the distal end of the pin to move relative to the drill shaft. In use, the main handle of the instrument is manipulated to subcutaneously introduce the drill into the metacarpal, metatarsal, or phalangeal base, and the pin handle is then moved relative to the main handle to introduce a pin into the bone until it extends through the medullary canal on either side of the fracture. Several pins may likewise be inserted to torsionally immobilization of the fracture.

19 Claims, 12 Drawing Sheets

U.S. PATENT DOCUMENTS

| | | | |
|---|---|---|---|
| 5,527,316 | 6/1996 | Stone et al. | 606/80 |
| 5,571,103 * | 11/1996 | Bailey | 606/62 |
| 5,591,207 | 1/1997 | Coleman | 606/232 |
| 5,609,595 * | 3/1997 | Pennig | 606/73 |
| 5,624,446 | 4/1997 | Harryman, II | 606/96 |
| 5,624,447 | 4/1997 | Myers | 606/96 |
| 5,681,333 | 10/1997 | Burkhart et al. | 606/148 |
| 5,702,475 * | 12/1997 | Zahedi | 623/22 |
| 5,709,682 * | 1/1998 | Medoff | 606/60 |
| 5,720,749 | 2/1998 | Rupp | 606/79 |
| 5,766,179 | 6/1998 | Faccioli et al. | 606/98 |
| 5,788,699 | 8/1998 | Bobst et al. | 606/80 |
| 5,851,208 | 12/1998 | Trott | 606/80 |
| 5,893,850 * | 4/1999 | Cachia | 606/72 |
| 6,074,392 * | 6/2000 | Durham | 606/67 |

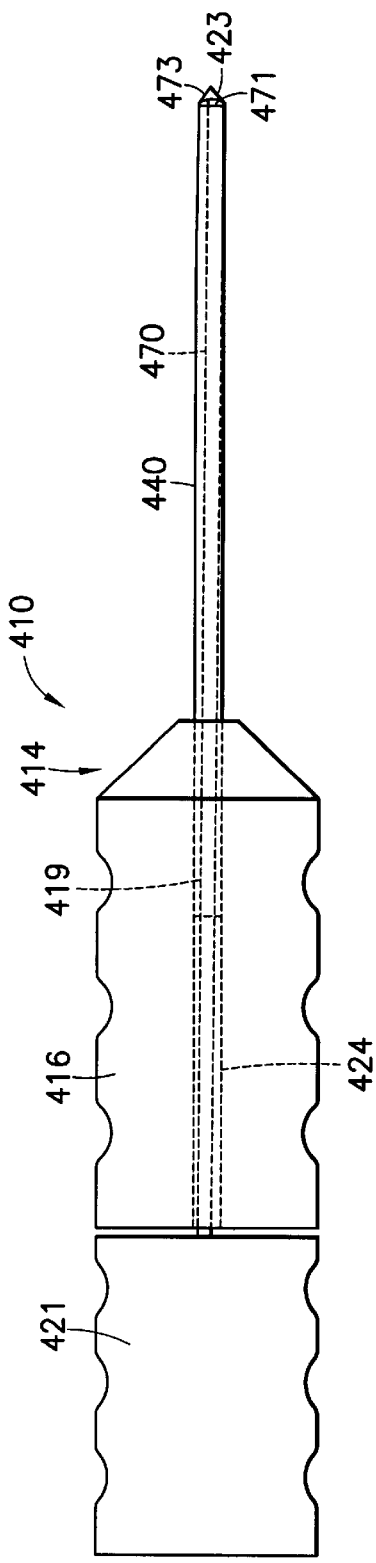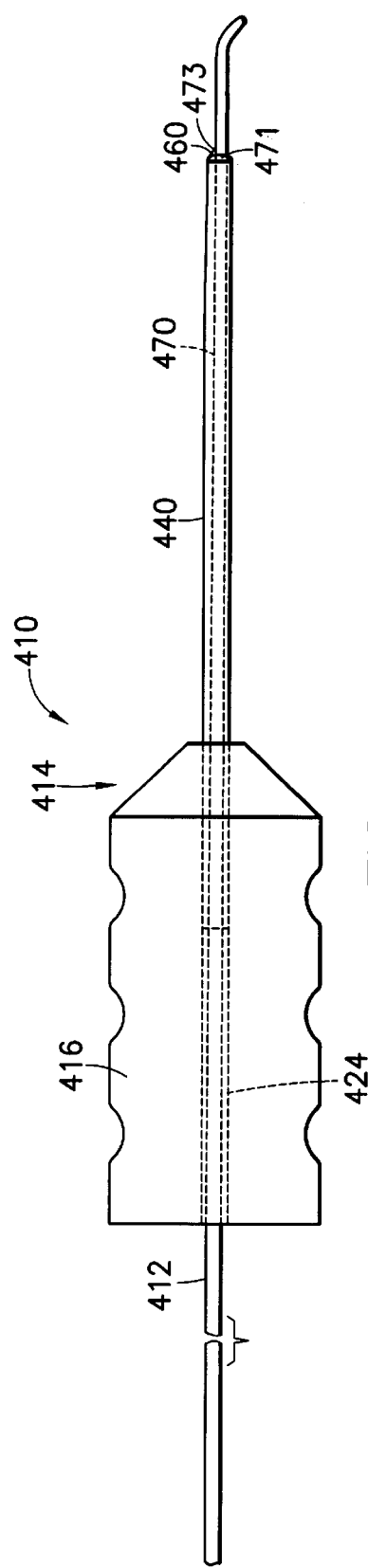

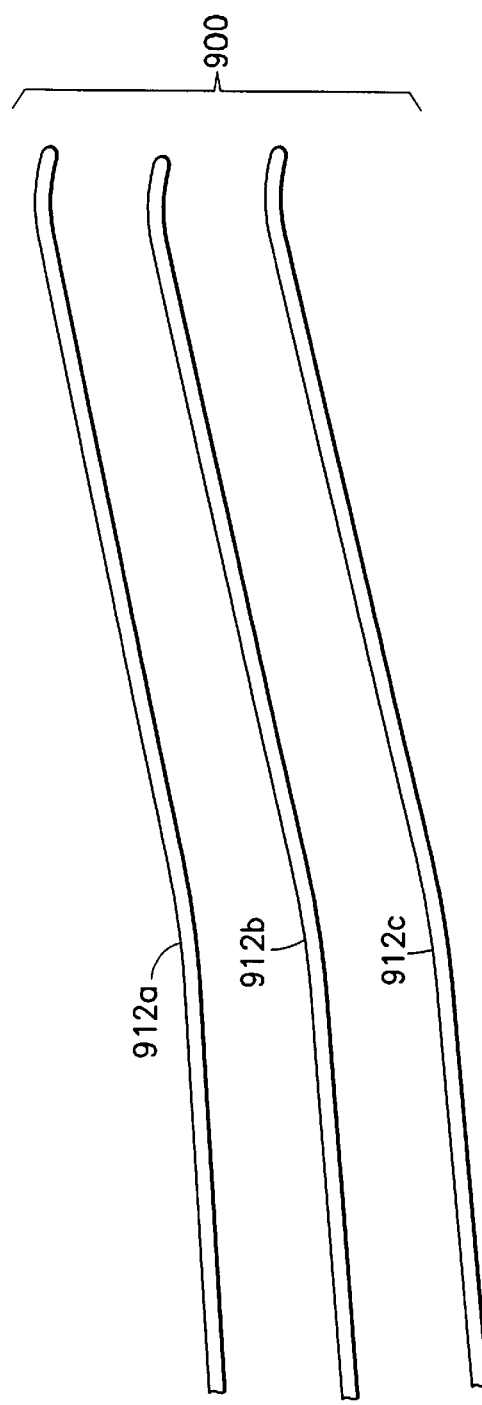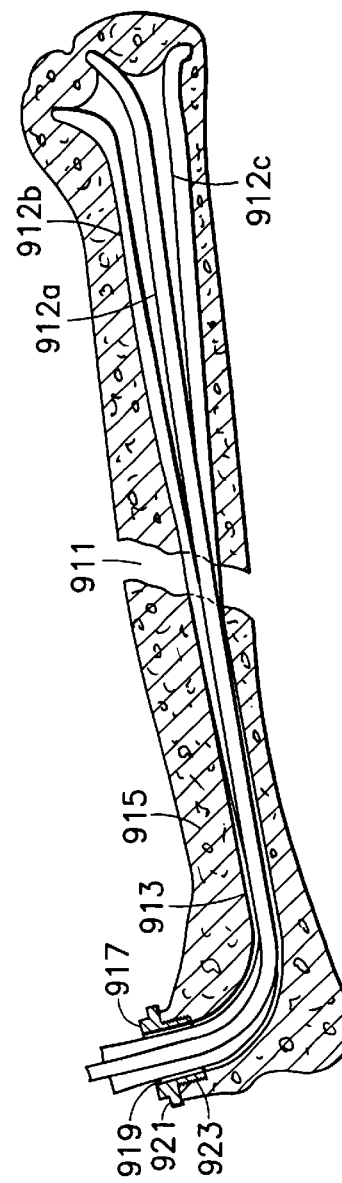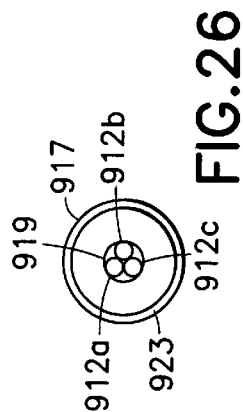

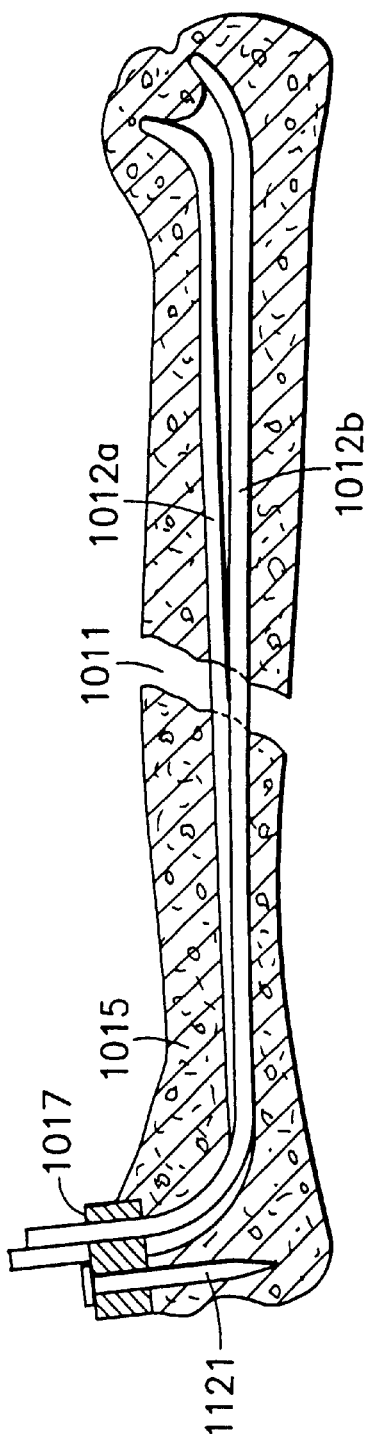
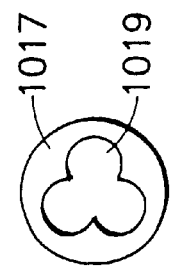
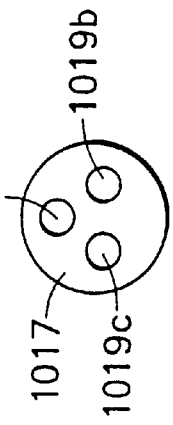

FRACTURE FIXATION SYSTEM

This application is a continuation-in-part of U.S. Ser. No. 09/150,792, filed Sep. 10, 1998, now U.S. Pat. No. 6,200,321, which is hereby incorporated by reference herein in its entirety.

BACKGROUND OF THE INVENTION

1. Field of the Invention

This invention relates broadly to a system for bone fracture fixation. More particularly, this invention relates to an improved method and a related system for fixation of fractures of relatively small bones.

2. State of the Art

Metacarpal fractures are very common. Immobilization of the metacarpal bone on either side of the fracture is imperative for proper healing. However, the location of the fracture presents several difficulties to ideal immobilization.

The most frequently used treatments for immobilizing the fracture are splinting and casting. However, due to the location of the metacarpal bones, these treatments fail to maintain proper fracture reduction in the metacarpal bones. Strong fixation is possible with techniques using plates, fixation screws, and fixation pins attached to the affected bones through operative treatment. While these types of fracture reduction devices are commonly used in larger bone fractures, e.g., ulnar, tibial, or femoral fractures, such operative treatment generally implies a formidable incision and exposure of the fracture site. Therefore, these techniques are often judged to be too invasive for the relatively small and fragile metacarpal bones.

An alternative less invasive technique has been used in which a small incision is made in the skin proximal the metacarpal bone, a boring tool is inserted through the incision and is used to drill a small hole into the metacarpal bone, the boring tool is removed, and then the physician feeds the pin through the incision and into the small unseen bore in the bone. However, feeding the pin through the skin is a blind operation with no manner provided for indicating to the physician the relative location of the pin and the small hole bored in the bone. As such, the technique is objectionable to both physician and patient as blind feeding can result in exacerbating damage to the surrounding tissue. In addition, the implanted pin fails to provide torsional fixation for fractures which need to be rotationally immobilized.

Furthermore, similar problems exist with respect to metatarsal and phalangeal fractures.

SUMMARY OF THE INVENTION

It is therefore an object of the invention to provide a fracture fixation system which permits stable fixation for metacarpal, metatarsal, and phalangeal fractures, and fractures of similar bones.

It is another object of the invention to provide a fracture fixation system which provides internal percutaneous fixation for metacarpal, metatarsal, and phalangeal fractures, and fractures of similar bones.

It is also an object of the invention to provide a fracture fixation system which provides torsional stabilization for metacarpal, metatarsal, and phalangeal fractures, and fractures of similar bones.

It is a further object of the invention to provide a fracture fixation system which provides a fixation system which is adjustable in size for metacarpal, metatarsal, and phalangeal fractures, and fractures of similar bones.

It is an additional object of the invention to provide a fracture fixation system which when compared to prior art operative treatment is relatively noninvasive.

In accord with these objects, which will be discussed in detail below, a fracture fixation system is provided. For simplicity, the fracture fixation system generally will be described with reference to the metacarpal bones, although it also applies to metatarsal bones, phalangeal bones, similar bones. The system facilitates the insertion of one or more fixation pins into the medullary canal of a fractured metacarpal bone for stable bone fixation.

According to one embodiment of the invention, the system includes a fixation pin and an instrument for implanting the fixation pin. According to a first embodiment of the invention, the instrument includes a main handle and a pin handle movable relative to the main handle. The main handle includes a proximal end, a distal end, and a longitudinal slot having an opening in the distal end of the handle. A boring shaft (drill) is coupled to the distal end of the main handle. The boring shaft includes a distal boring tip and a pin guide proximally adjacent the boring tip for guiding the fixation pin into the medullary canal. The pin guide is preferably a groove in the shaft. The pin handle is shaped and sized to slidably move within the longitudinal slot, and may be provided with finger grips and a distal bore into which the fixation pin is received. The fixation pin preferably includes a substantially straight proximal and central portions, and a curved distal portion having a preferably blunt tip. Initially, the curved distal portion rests within the pin guide of the boring shaft. It will be appreciated that relative distal movement of the pin handle within the slot of the main handle causes the distal portion of the fixation pin to move through and beyond the pin guide.

In use, the main handle of the instrument is manipulated to subcutaneously introduce the boring shaft into the base of the fractured metacarpal bone in a hand of a patient. Once the tip of the shaft has entered the base of the metacarpal bone, it is left in position, and the pin handle is moved distally relative to the main handle to force the distal portion of the fixation pin into the bone. The pin thereby enters the natural hollow of the medullary canal of the bone. The main handle is then moved proximally relative to the pin handle to remove the boring shaft from the hand of the patient, and to disengage the main handle from the pin handle. The pin handle is then further moved to force the pin through the natural hollow of the medullary canal of the fractured metacarpal bone until it extends through the canal on either side of the fracture and provides the necessary immobilization of the fractured bone. The blunt tip prevents the pin from piercing the distal end of the metacarpal bone. Finally, the proximal end of the pin is bent, cut, and preferably subcutaneously seated.

According to other embodiments of the instrument of the fracture fixation system, the instrument includes a shaft handle having at its distal end a boring shaft coupled thereto. The boring shaft has an internal pathway and a distal exit. The shaft handle includes a throughbore in communication with the internal pathway of the shaft and through which the fixation pin can be received. The handle permits manual subcutaneous insertion and rotation of the shaft to provide the tip of the boring shaft into the metacarpal bone. The distal exit may be either axial or lateral. An awl member may be optionally provided in the throughbore and internal pathway and extended to the distal exit of the shaft for shaft insertion into the metacarpal bone, and then removed for extending the fixation pin through the internal pathway and distal exit of the shaft. According to another embodiment, the pathway of the boring shaft is provided with a proximal lateral entrance, and exits either laterally or axially at the distal end of the shaft.

In addition, the fixation pin may alternatively be adapted to be self-guiding to follow the medullary canal. The proximal and central portions of the pin are relatively straight and sufficiently stiff (providing fixation, yet permitting forced insertion into bone). Adjacent the distal end, a reduced diameter portion is provided which permits the distal end to easily bend relative to the central portion and follow the medullary canal. Preferably, a coil is provided about the reduced diameter portion to provide the pin with an apparently constant diameter.

Furthermore, the fixation pin may be particularly adapted for use in relatively small medullary canals such as that found in the phalanges, i.e., the fixation pin may have a relatively small distal diameter. In order to permit such a fixation pin to be used with the same pin handle as used for fixation pins adapted for metacarpal and metatarsal bones, the fixation pin includes a proximal end having a uniform diameter, and a distal end having a relatively smaller diameter, and a tapered or stepped portion therebetween.

According to yet another embodiment of the invention, the fixation system includes a plurality of fixation pins and an instrument for sequentially implanting at least two of the fixation pins into the medullary canal of a fractured bone. The instrument is substantially as described above, with each of the pins separately providable into the pin handle. The pins may have the same diameter or may be provided as a set to include pins of various diameters. Each individual pin is smaller than the medullary canal of the bone, yet when implanted in combination with one or more others of the pins provides a fixation system which approximates the inner diameter of the medullary canal in order to provide the required fixation. Each individual pin is implanted as described above, and at least two pins are implanted to stabilize the fracture. A collet is preferably provided over the proximal ends of the pins to couple the pins together and thereby prevent relative rotation of the pins. In addition, the collet is preferably adapted to be coupled to the bone to immobilize the proximal ends of the pins relative to the bone. As such, the fixation system provides torsional stabilization to the fracture.

Additional objects and advantages of the invention will become apparent to those skilled in the art upon reference to the detailed description taken in conjunction with the provided figures.

BRIEF DESCRIPTION OF THE DRAWINGS

FIG. 18 is a side elevation of a second embodiment of the instrument of the fracture fixation system of the invention shown with an inner awl component extending through the shaft;

FIG. 19 is a side elevation of the second embodiment of the instrument shown a fixation pin extending through the shaft in place of the inner awl component;

FIG. 24 is side elevation of a set of fixation pins according to a sixth embodiment of the invention;

FIG. 25 is a section view of a torsionally stabilized fixation system according to the sixth embodiment of the invention;

FIG. 26 is a top view of a collet according to the sixth embodiment of the invention;

FIG. 27 is a section view of a torsionally stabilized fixation system according to a seventh embodiment of the invention;

FIG. 28 is a top view of a first collet according to the seventh embodiment of the invention; and FIG. 29 is a top view of a second collet according to the seventh embodiment of the invention.

DETAILED DESCRIPTION OF THE PREFERRED EMBODIMENTS

Figure 1:
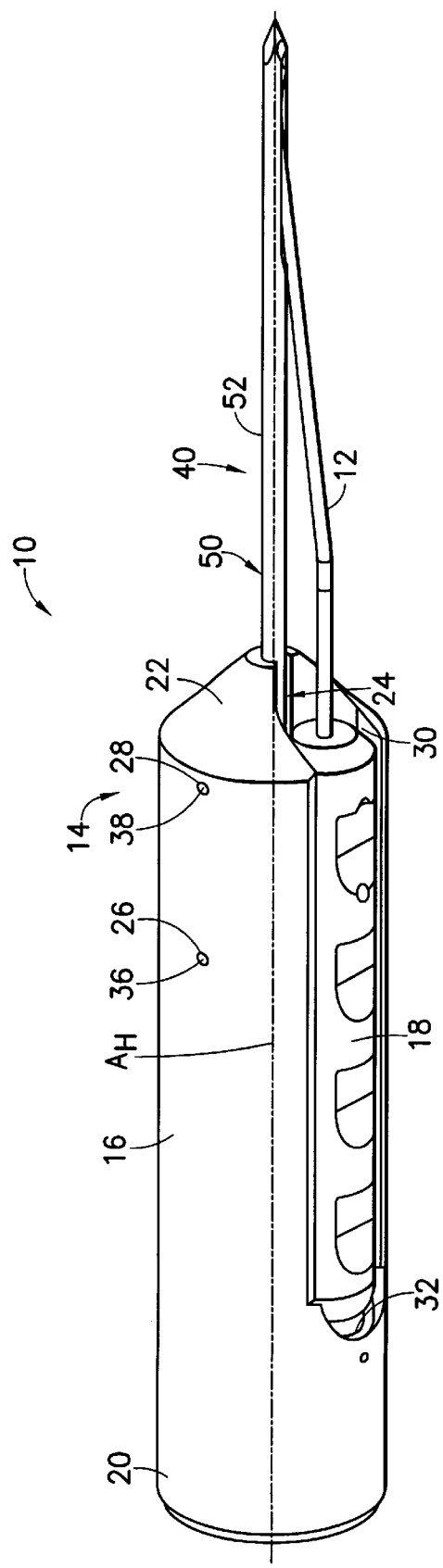
FIG. 1 is a perspective view of a first embodiment of a fracture fixation system.

As stated above, the invention will be described with reference to a fracture in a metacarpal bone, although it also applies to fixating fractures in metatarsal and phalangeal bones. Turning now to FIGS. 1 through 4, a metacarpal fracture fixation system 10 for the insertion of a fixation pin into the medullary canal of a fractured metacarpal bone is shown. The system 10 includes a fixation pin 12 and an instrument 14 for implanting the fixation pin. According to a first embodiment of the invention, the instrument 14 includes a main handle 16 provided with a stationary drill 40, and a pin handle 18 movable relative to the main handle for implanting the fixation pin 12.

Figure 9:
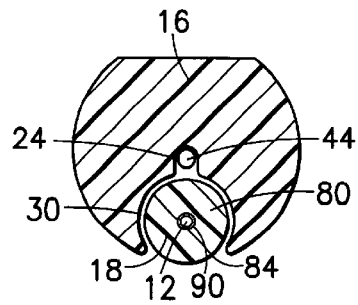
FIGS. 9, 10, and 11 are cross-section views through lines 9—9, 10—10, and 11—11, respectively, in FIG. 2.
Figure 10:
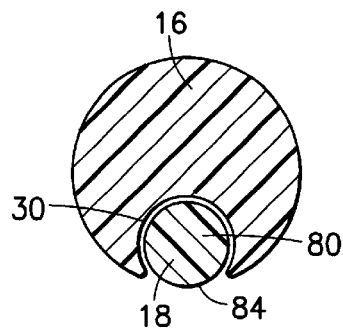
Figure 11:
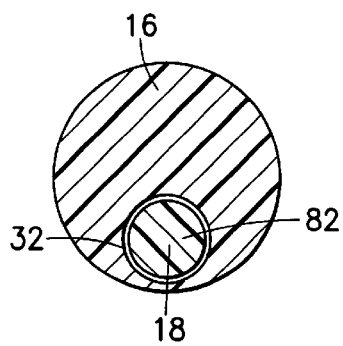

The main handle 16 includes a proximal end 20, a preferably frustoconical distal end 22, a longitudinal drill slot 24 (seen best in FIGS. 1 and 9) preferably in alignment with a longitudinal axis $A_H$ of the main handle 16, two radial bores 26, 28 which extend into the drill slot 24, and a pin handle slot 30 and pin handle bore 32 (seen best in FIGS. 11 and 15), both for receiving the pin handle 18, as described below. The main handle 16 is preferably chamfered about the pin handle slot 30, and also preferably includes a plurality of indentations 34 to facilitate engagement of the main handle 16 by the fingers of one hand (or both hands) of the physician. The main handle is preferably molded from plastic, e.g., ABS, nylon, polycarbonate, or polyethylene, but may be machined from a Delrin™ rod or a similar material.

The drill 40 is provided in the longitudinal drill slot 24. The drill 40 includes a shaft 42 having a proximal end 44 provided with two lateral bores 46, 48 (FIG. 2), and a distal end 50 described in detail below. The drill 40 is fixed in the main handle 16 with two pins 54, 56 secured, preferably by interference fit, through the lateral bores 26, 28 in the main handle 16 and into the lateral bores 46, 48 in the shaft 42 of the drill 40. The drill 40 is preferably made from a stainless steel bar having a 0.125 inch diameter and a length of approximately 5.7 inches. Approximately 1.7 inches of the shaft is provided in the handle and approximately 4 inches of the shaft extend distally from the main handle 16.

Figure 13:
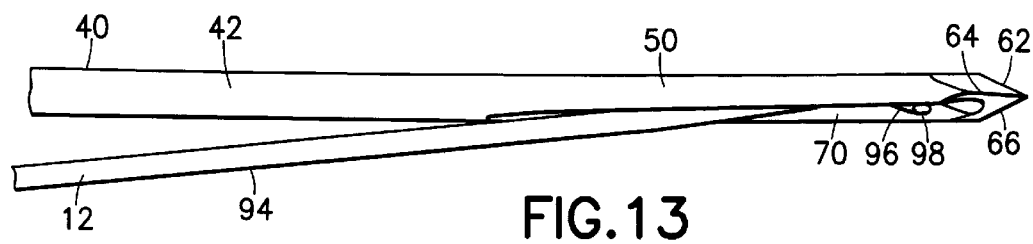
FIG. 13 is an enlarged perspective view of the distal end of the shaft and the fixation pin.

Referring to FIGS. 5 through 8, the distal end 50 of the shaft 42 of the drill 40 includes a boring tip 60 which preferably comprises three cutting edges 62, 64, 66 displaced 120° from each other about the boring tip and tapered to a point 68. The taper is preferably at approximately 13° relative to the longitudinal axis $A_S$. In addition, and according to a preferred aspect of the invention, the distal end 52 is provided with a lateral guiding groove 70 which guides the fixation pin 12. The guiding groove 70 includes a proximal sloped portion 72 and a distal curved deflecting portion 74. The sloped portion is preferably sloped such that a line $L_P$ perpendicular to a surface 76 of the sloped portion 70 is angled approximately 5° to 8° relative to a line Ls perpendicular to the axis $A_S$ of the shaft 42. The curved portion 74 preferably has a radius of approximately 0.50 inches. In a preferred embodiment, the guiding groove 70 preferably extends into the shaft 42 a groove depth $D_G$ of approximately 0.110 inches at the intersection of the sloped portion 72 and the curved portion 74, and preferably has a width $W_G$ of approximately 0.063 inches. The groove depth $D_G$ is preferably greater than the diameter of the pin 12 such that the combined diameters of the pin 12 and the shaft 42 at the guiding groove 70 does not exceed the outer diameter of the shaft (FIG. 13). The width $W_G$ is preferably 0.002–0.003 inch greater than the diameter of the pin so that the pin is accurately guided without binding.

Referring to FIGS. 1–4, 9–11, and 14–15, the pin handle 18 includes a distal portion 80 which is sized and shaped to slidably move within the pin handle slot 30 of the main handle 16, and a proximal portion 82 which is sized and shaped to slidably move within the pin handle bore 32 of the main handle 16. A lower area 84 of the distal portion 80 includes a plurality of indentations 86 which facilitates movement of the pin handle 18 relative to the main handle 16 by fingers of the physician. A distal end 88 of the pin handle 18 is chamfered and provided with a bore 90 into which the fixation pin 12 is secured, preferably by an interference fit. The pin handle 18, like the main handle 16, is also preferably molded from plastic, e.g., ABS, nylon, polycarbonate, or polyethylene, but may be machined from a Delrin™ rod or a similar material.

Figure 2:
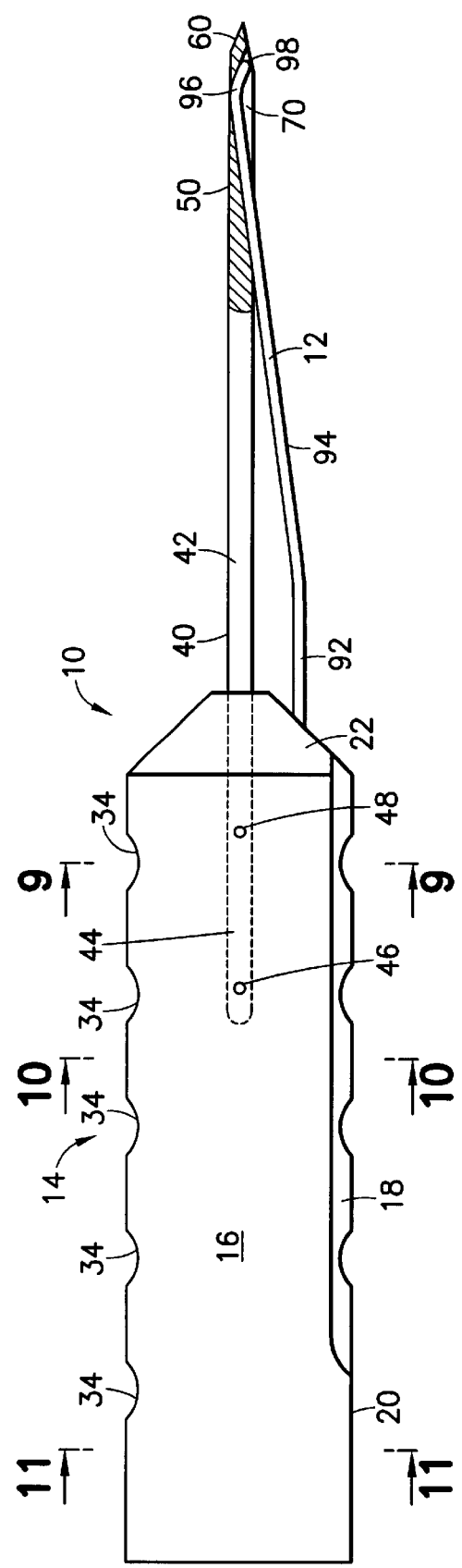
FIG. 2 is a side view of the first embodiment of the fracture fixation system with the distal end of a drill of the system shown in section.
Figure 3:
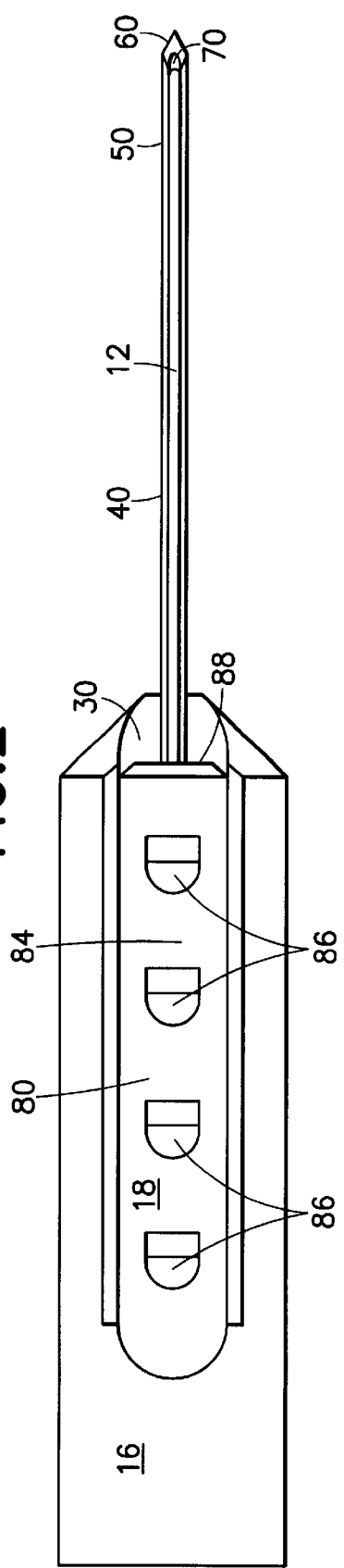
FIG. 3 is a bottom view of the first embodiment of the invention.
Figure 4:
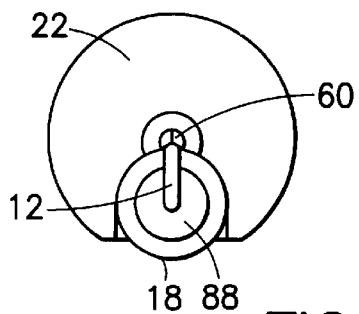
FIG. 4 is a distal end view of the fracture fixation system of the invention.
Figure 5:
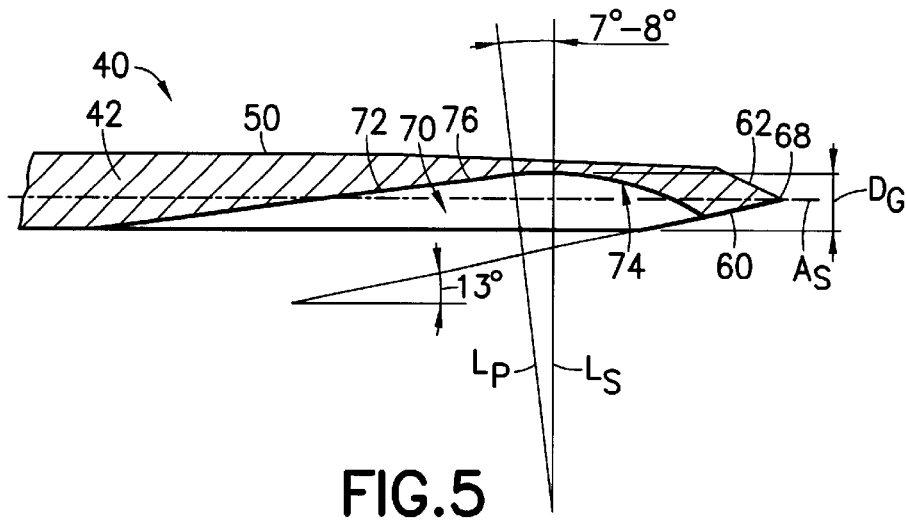
FIG. 5 is an enlarged section view of the distal end of the drill according to the first embodiment of the fracture fixation system of the invention.
Figure 6:
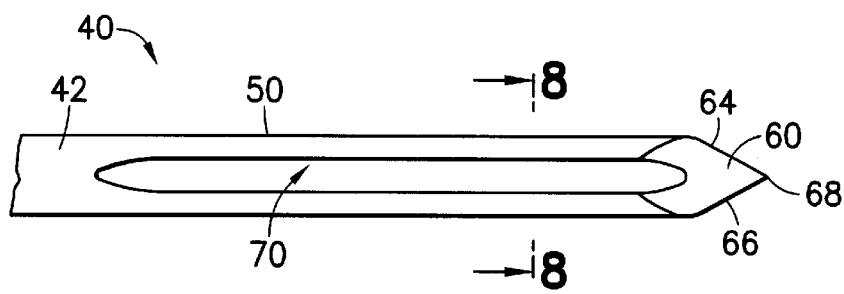
FIG. 6 is an enlarged bottom view of the drill of the distal end of the drill according to the first embodiment of the fracture fixation system of the invention.
Figure 7:
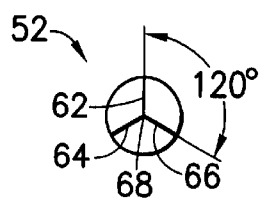
FIG. 7 is an enlarged distal end view of the drill of the according to the first embodiment of the fracture fixation system of the invention.
Figure 8:
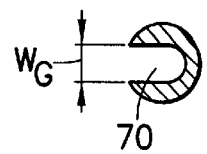
FIG. 8 is a cross-section through line 8—8 in FIG. 7.
Figure 12:
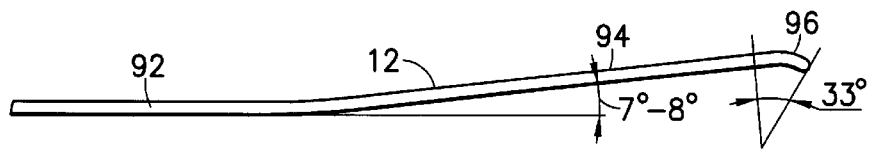
FIG. 12 is a side view of the fixation pin of the fracture fixation system of the invention.

As shown in FIGS. 2 and 12, the fixation pin 12 preferably includes a substantially straight proximal portion 92, the end of which is secured in the distal end 88 of the pin handle 18, a substantially straight central portion 94, which may optionally be angled relative to the proximal portion 92, and a curved, distal portion 96 having a preferably blunt tip 98. If the proximal portion 92 and central portion 94 are angled relative to each other, it is preferable that the angle be approximately 5°–8°. The distal tip 96 is preferably curved about an approximately 0.50 inch radius for approximately 33° degrees. The fixation pin 12 is preferably made from a solid metal wire material, e.g., stainless steel. It will be appreciated that the fixation pin must have a stiffness sufficient to immobilize the bone fracture, yet be resiliently flexible enough to permit the pin 12 to be sufficiently bent for insertion into the medullary canal of the bone, as described below. Therefore, the system 10 may include a plurality of fixation pins 12 having various diameters. One preferred fixation pin 12 preferably has a length of approximately 6.0 inches, with approximately 0.70 inches secured in the distal bore 90 of the pin handle 18, and a diameter of approximately 0.060 inches.

Figure 14:
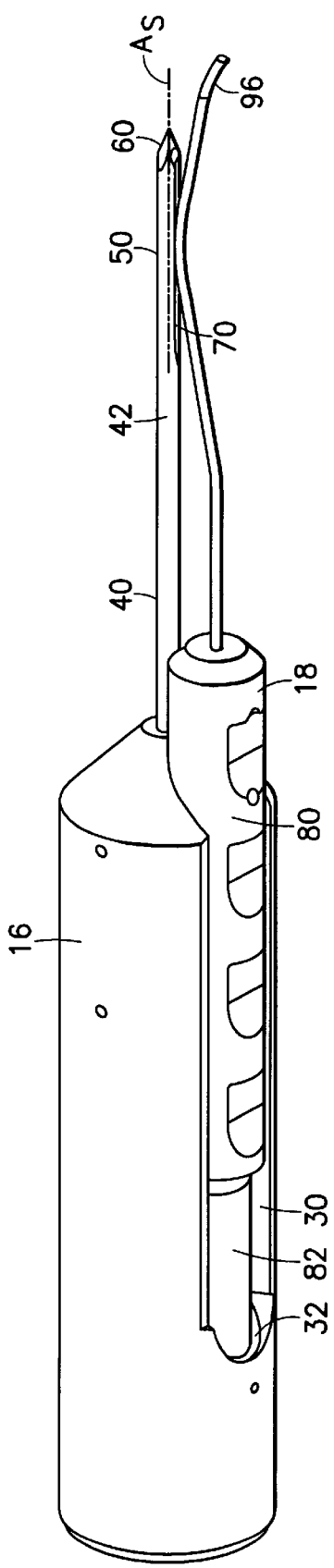
FIG. 14 is a perspective view of the system of the first embodiment of the invention with the pin handle and fixation pin shown in a partial distal configuration relative to the main handle and drill.
Figure 15:
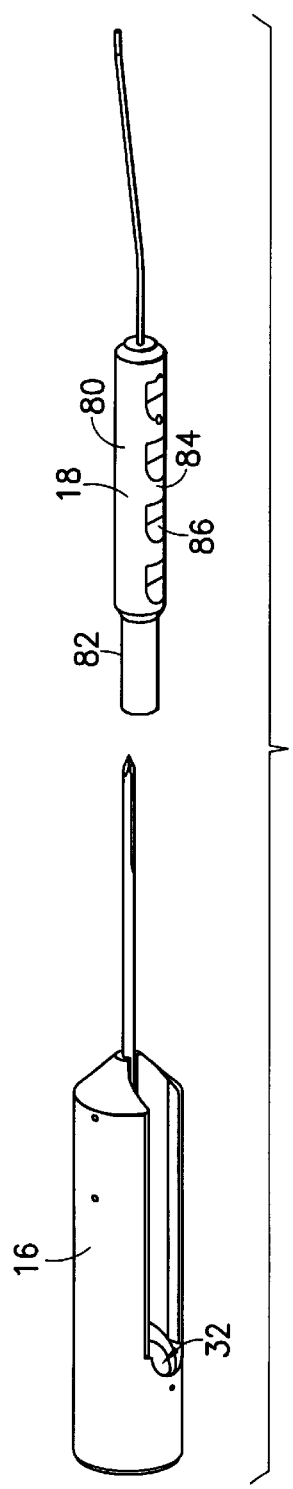
FIG. 15 is a perspective view of the system of the first embodiment of the invention with the pin handle and fixation pin shown separated from the main handle and drill.

Referring now to FIGS. 1, 13, and 14, the fixation pin 12 is positioned in the pin handle 18, and the pin handle 18 in the main handle 16 such that the curved distal portion 96 of the fixation pin 12 rests within the guiding groove 70 of the shaft 42 of the drill 40, and the distal portion 96 does not extend beyond the circumferential profile of the shaft. Referring to FIG. 14, movement of the pin handle 18 within the pin handle slot 30 and pin handle bore 32 of the main handle 16 distally relative to the main handle causes the distal portion 96 of the fixation pin 12 to move relative to the shaft 42 of the drill 40, through the guiding groove 70, and to extend beyond the boring tip 60, preferably at an angle relative to the axis of the shaft $A_S$. The pin handle may be moved to extend the distal end of the pin preferably at least one quarter inch, and more preferably one to three inches, beyond the distal end of the shaft while remaining coupled to the main handle. Moreover, it will be appreciated that no impediment is present which inhibits the pin handle 18 from being moved distally relative to the main handle 16, or the main handle moved proximally relative to the pin handle. As such, as shown in FIG. 15, the pin handle may be separated from the main handle.

In use, the main handle 16 of the instrument 14 is manipulated by hand to subcutaneously introduce the boring tip 60 of the drill 40 into the base of a fractured metacarpal bone. Once the boring tip 60 of the drill 40 has entered the base of the metacarpal bone, the drill is oriented such that the guiding groove 70 is oriented to guide the fixation pin 12 through the natural hollow of the medullary canal of the metacarpal bone. The pin handle 18 is then manually moved relative to the main handle 16 to force the curved distal portion 96 of the fixation pin 12 into the bone. The main handle 16 is then moved proximally relative to the pin handle 18 to remove the drill 40 from the bone and disengage the main handle from the pin handle. This is performed while preferably maintaining the pin handle, and the fixation pin which is attached thereto, at its present location. The pin handle is then manipulated to move the pin through the canal of the fractured metacarpal bone until the pin extends on either side of the fracture and provides the necessary immobilization of the fractured bone. It will be appreciated that the complementary shape of the fixation pin and groove (e.g., the 5°–8° angle of the central portion of the pin relative to the proximal portion of the pin is substantially similar to the 5°–8° angle of the proximal portion of the groove, and the 0.50 inch radius of curvature of the distal portion of the pin is substantially the same as the 0.50 inch radius of curvature of the distal portion of the groove), facilitates directing the fixation pin into the medullary canal. The blunt tip 98 of the fixation pin 12 prevents the pin from piercing the distal end of the metacarpal bone. Finally, once the physician determines that the fixation pin is properly fixating the fractured bone, the pin handle 18 may then be manipulated to bend the fixation pin 12 adjacent the cutaneous entrance hole, the pin is cut, and the cut end is either subcutaneously seated or covered with a bandage outside the skin. After fracture healing, the fixation pin is extracted, e.g., with pliers, from the bone and then discarded. The cutaneous entrance hole is then permitted to heal.

It will be appreciated that the fracture fixation system of the invention provides substantial fixation to a metacarpal fracture, yet does not require an unduly invasive procedure or a large number of steps. In addition, the procedure reduces the number of physician "hands", relative to invasive surgery, required to sufficiently immobilize a fracture for proper healing.

Figure 16:
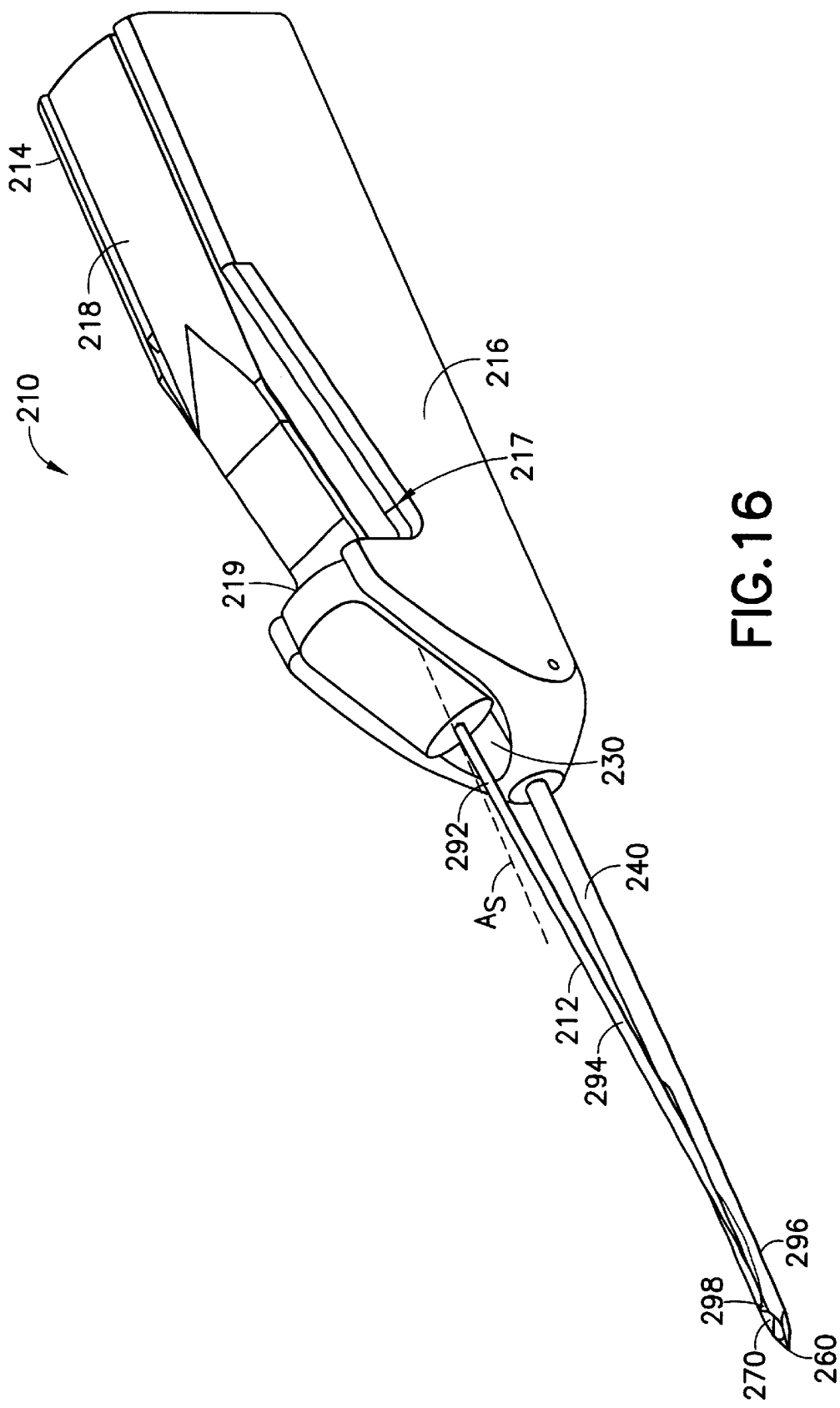
FIG. 16 is a perspective view of a second embodiment of the fracture fixation system according to the invention.

Turning now to FIG. 16, a second embodiment of an instrument 214 for a fracture fixation system 210, substantially similar to the first embodiment (with like parts having numbers incremented by 200) is shown. The instrument 214 includes a shaft 240 having a distal guiding groove 270 and sharp boring end 260. The shaft 240 includes a shaft handle 216 for manipulating the shaft. The shaft handle 216 includes a slot 230 into which a pin handle 218 is slidably received. The slot 230 preferably slopes downward toward the shaft. The shaft handle 216 is further provided with grips 217 for stably gripping the shaft handle 216 in a hand of the physician. The pin handle 218 includes a ridge 219 which may be used to leverage relative distal movement of the pin handle through the slot 230 of the shaft handle 216. The pin handle 218 and the shaft handle 216 are preferably positively engagable relative to each other, e.g., with a snap fit, and may be disengaged by sufficient force on the ridge 219 of the pin handle to move the pin handle relative to the shaft handle. Release may also provide tactile indication that the handles have disengaged and a tip 298 of the pin 212 has moved slightly ahead of the boring tip 260 of the shaft 240. The slope of the slot 230 permits a fixation pin 212 provided axial within the pin handle to be directed toward and through the guiding groove 270 when the pin handle is located in the slot 230 and moved within the slot. The pin 212 is preferably angled relative to a longitudinal axis $A_P$ of the shaft handle 216 such that the pin 212 is directed toward the shaft 240. Preferably, the fixation pin 212 includes a proximal portion 292 and a central portion 294 which are coaxially aligned, and a distal portion 296 provided with the blunt, preferably curved tip 298. In operation, after the boring end 260 of the shaft 240 has been inserted into the metacarpal bone, the pin handle 218 is moved distally relative to the shaft handle to move the pin 212 through the guiding groove 270 and into the medullary canal of the fractured bone. The shaft handle 216 is then removed from the pin handle 218, and the pin handle is manipulated to further extend the fixation pin through the medullary canal of the bone and fixate the bone. After the physician is assured that the fixation pin provides desirable fixation of the fracture (i.e., that it has sufficient diametric fit within the medullary canal), the pin is bent and cut at the skin surface.

Figure 17:
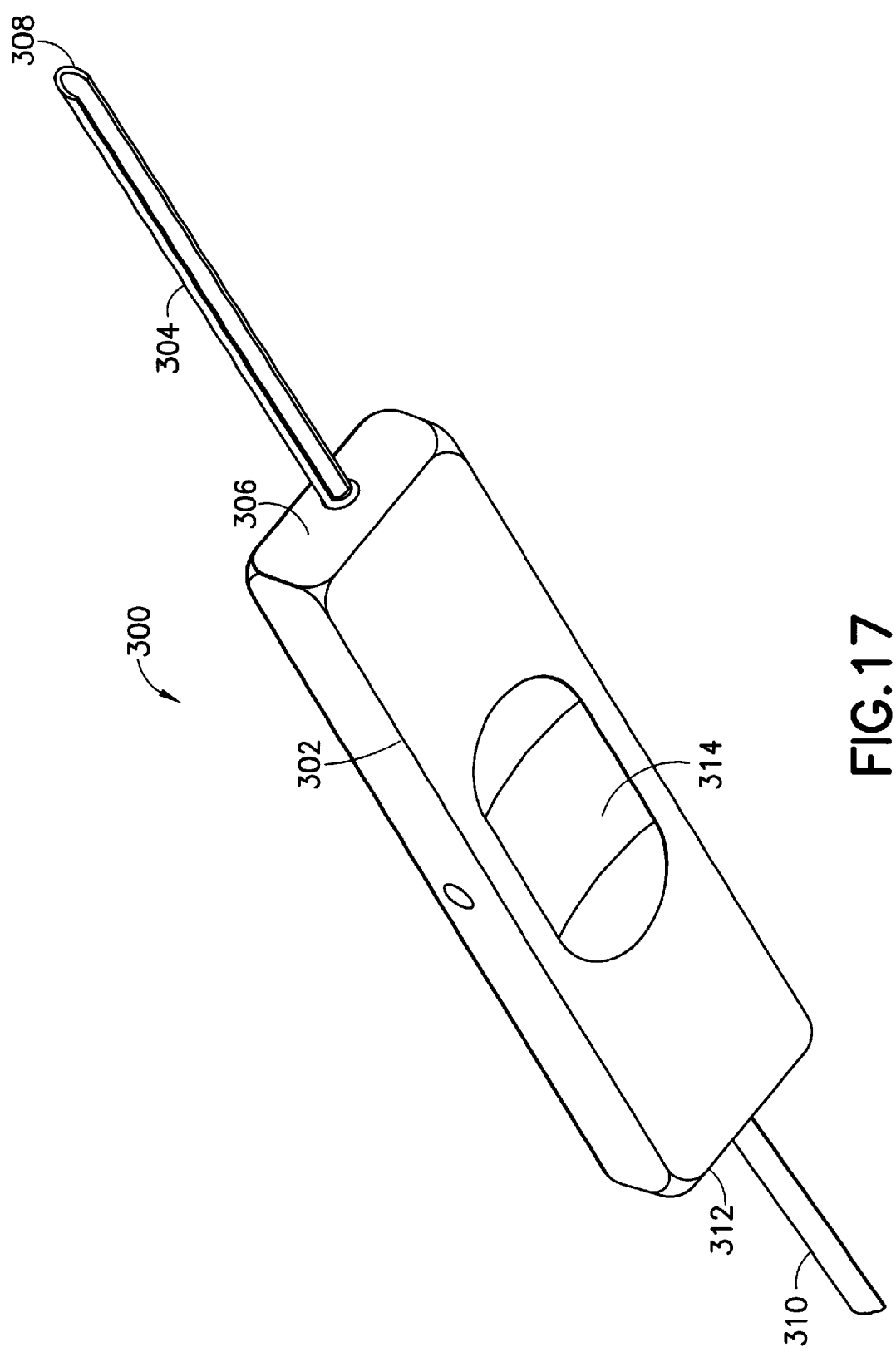
FIG. 17 is a perspective view of a supplemental re-guiding tool for use in the fracture fixation according to the invention.

It will be appreciated that after inserting a fixation pin into the medullary canal (but prior to bending and cutting the pin), in certain circumstances, the physician may determine that the inserted pin is unsuitably sized for the particular patient, and that a fixation pin having a different diameter is required. To that end, a set of fixation pins including fixation pins having distal portions of various sizes (e.g., substantially 0.060, substantially 0.051 inch, substantially 0.045 inch, substantially 0.038 inch, and substantially 0.035 inch) is provided for use by the physician. However, if the pin presently inserted in the hand is removed from the hand for replacement, the entry hole in the bone will be difficult to relocate. Therefore, referring to FIG. 17, a supplemental re-guiding tool 300 may be provided in the system of the invention. The re-guiding tool 300 includes a handle 302, a slotted shaft 304 extending from one end 306 of the handle and having an inclined leading edge 308, and a tubular bending portion 310 extending from the other end 312 of the handle. The handle 302 is preferably further provided with a depression 314 into which the thumb of the physician may seat and which thereby facilitates gripping the handle.

The slotted shaft 304 of the re-guiding tool 300 may be extended over the fixation pin which the physician wants to replace, through the entry hole in the hand, and into the hole in the bone. The inclined leading edge 308 facilitates insertion of the shaft through the wound of the hand with minimal trauma to the area. It will be appreciated that the slotted shaft design provides a less traumatic manner of maintaining a pathway from the entry hole in the skin to the bone than reinserting the distal end of the boring shaft (drill). The fixation pin may then be removed, while the slotted shaft 304 acts as a guide for the replacement pin. Once the proper fixation pin has finally been determined, the pin is cut and the re-guiding tool 300 may be reversed and the bending portion 310 may be extended over the cut pin and used to leverage the bending of the pin for subsequent subcutaneous seating. While the guide tool 300 is most appropriately used with the first and second embodiments of the invention (which are provided with lateral pin guides), it will be appreciated that the guide tool may also be used with any of the following embodiments.

Turning now to FIG. 18, a third embodiment of an instrument 414 for a fracture fixation system 410 according to the invention is shown. The instrument 414 includes a shaft handle 416 having an axial throughbore 424 and a boring shaft 440 coupled in the distal end thereof. The shaft 440 is cannulated; i.e., the shaft 440 is provided with an internal pathway 470, and preferably includes a distal tip 460 with an axial pathway exit 471 and a preferably sharp annular cutting edge 473. The axial throughbore 424 and internal pathway 470 are in communication with each other and preferably axially aligned. A rod-like awl 419, provided with a proximal handle 421, is extendable through and removable from the pathway 470. The awl 419 preferably has a length such that when the handle 421 of the awl is seated flushly against the shaft handle 416, the tip 423 of the awl extends through the pathway exit 471 and operates as a boring tip. The inner awl and shaft may be locked together for insertion into the bone. The awl is then unlocked and removed from the internal pathway 470 to permit a fixation pin 412 to be fed through the pathway 470 and out the pathway exit 471 (FIG. 19).

In use, the awl handle 421 and shaft handle 416 is used to insert the tip 423 of the awl 419 and the tip 460 of the shaft 440 into the metacarpal bone. The awl handle 421 is then removed from the pathway 470, and the fixation pin 412 is maneuvered through the pathway and into the medullary canal. Once the fixation pin is sufficiently extended in the medullary canal to fixate the bone on either side of the fracture, the main handle 416 is proximally removed from over the pin 412. The pin may then be further manipulated, and is finally cut at the desired length.

Figure 20:
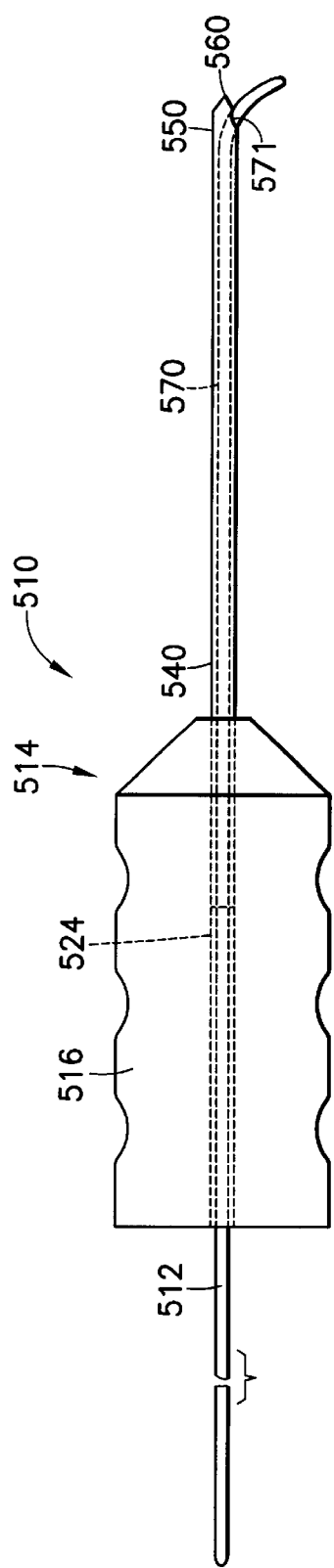
FIG. 20 is a side elevation of a third embodiment of the instrument of the fracture fixation system of the invention.

Referring now to FIG. 20, a fourth embodiment of an instrument 514 for a fracture fixation system 510 is shown. The instrument 514 includes a main handle 516 having a throughbore 524 and a boring shaft 540 coupled in the distal end thereof. The boring shaft 540 is cannulated and, at its distal end 550 includes a sharp boring distal tip 560 and a lateral pathway exit 571. A rod (not shown, but similar to the awl described with respect to the second embodiment) may be provided within the pathway 570 such that it closes the pathway exit 571 and thereby facilitates insertion of the shaft 540 into the bone. The rod, if provided, is then removed. A fixation pin 512 is then extended through the pathway 570 and into the medullary canal of the metacarpal bones.

Figure 21:
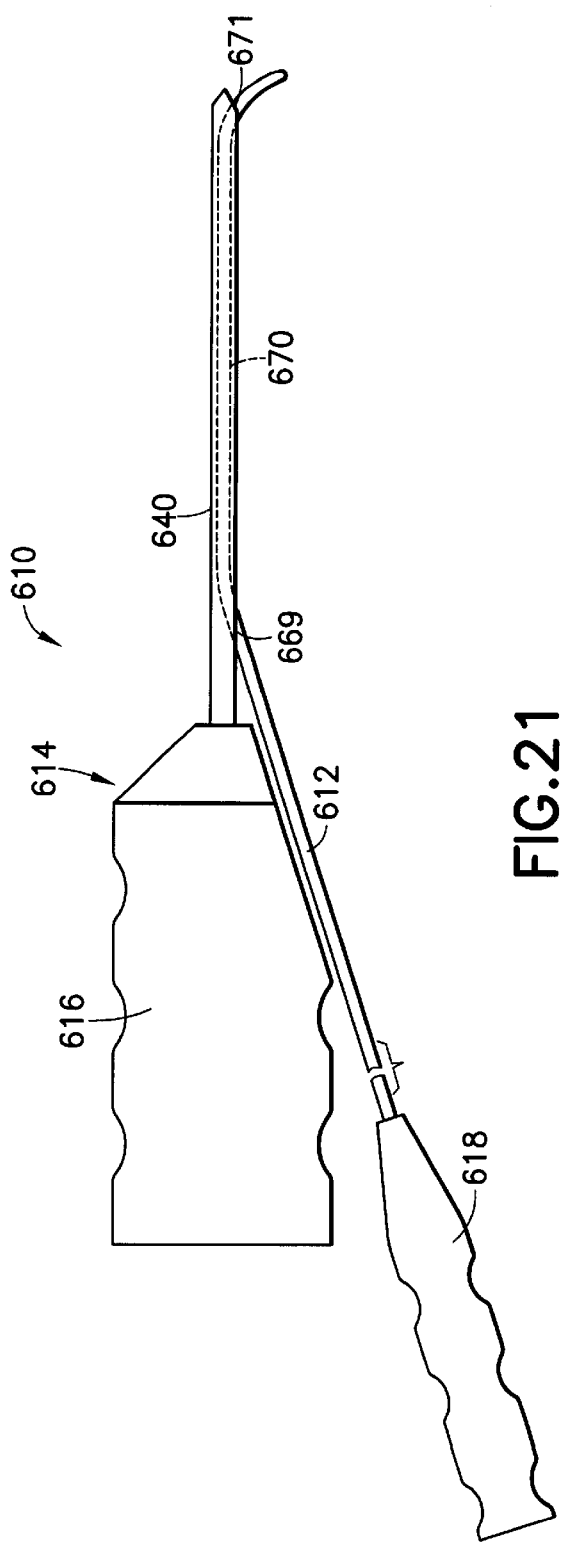
FIG. 21 is a side elevation of a fourth embodiment of the instrument of the fracture fixation system of the invention.

Turning now to FIG. 21, a fifth embodiment of an instrument 314 for a fracture fixation system 610 is shown. The instrument 614 includes a cannulated boring shaft 640 preferably provided with a proximal shaft handle 616, and a fixation pin 612 optionally having a pin handle 618 coupled to its proximal end. The cannulated shaft 640 includes a proximal lateral pin entry 669 into an axial pathway 670 of the shaft 640, and a distal lateral pathway exit 671 oriented to guide the pin into the medullary canal. Optionally, the pathway exit 671 may be axially aligned with the pathway 670 for axial guidance of the pin. After the shaft 640 has been inserted into the metacarpal bone, the pin 612 manipulated through the shaft 640 and into the canal of the fractured bone to fixate the bone. Where no pin handle is provided, the shaft 640 and shaft handle 616 are then proximally withdrawn over the pin 612, and the pin is manipulated such that it is sufficiently inserted, bent, and finally cut to the desired length. Where the optional pin handle 618 is utilized, the shaft 640 is moved proximally over the pin 612 toward the pin handle 618 such that the pin may be further manipulated and cut to the desired length.

Figure 22:
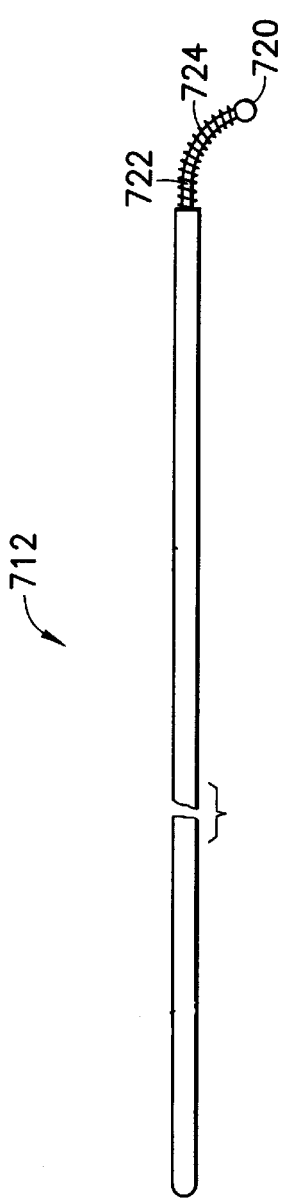
FIG. 22 is an alternative embodiment of the fixation pin of the of the fracture fixation system of the invention.

Turning now to FIG. 22, the fixation pin used in each of the above embodiments may be alternatively configured. For example, the fixation pin 712 may be provided with a narrowed portion 722 (i.e., a reduced diameter) adjacent the tip 720 about which a coil 724 is preferably positioned. This configuration is provided to permit the distal end 718 of the fixation pin to more easily bend and permit the fixation pin to preferably be self-guiding to follow the medullary canal. In addition, as an alternative to stainless steel, the pin 712 may be made from titanium, or another structurally supportive biocompatible material.

Figure 23:
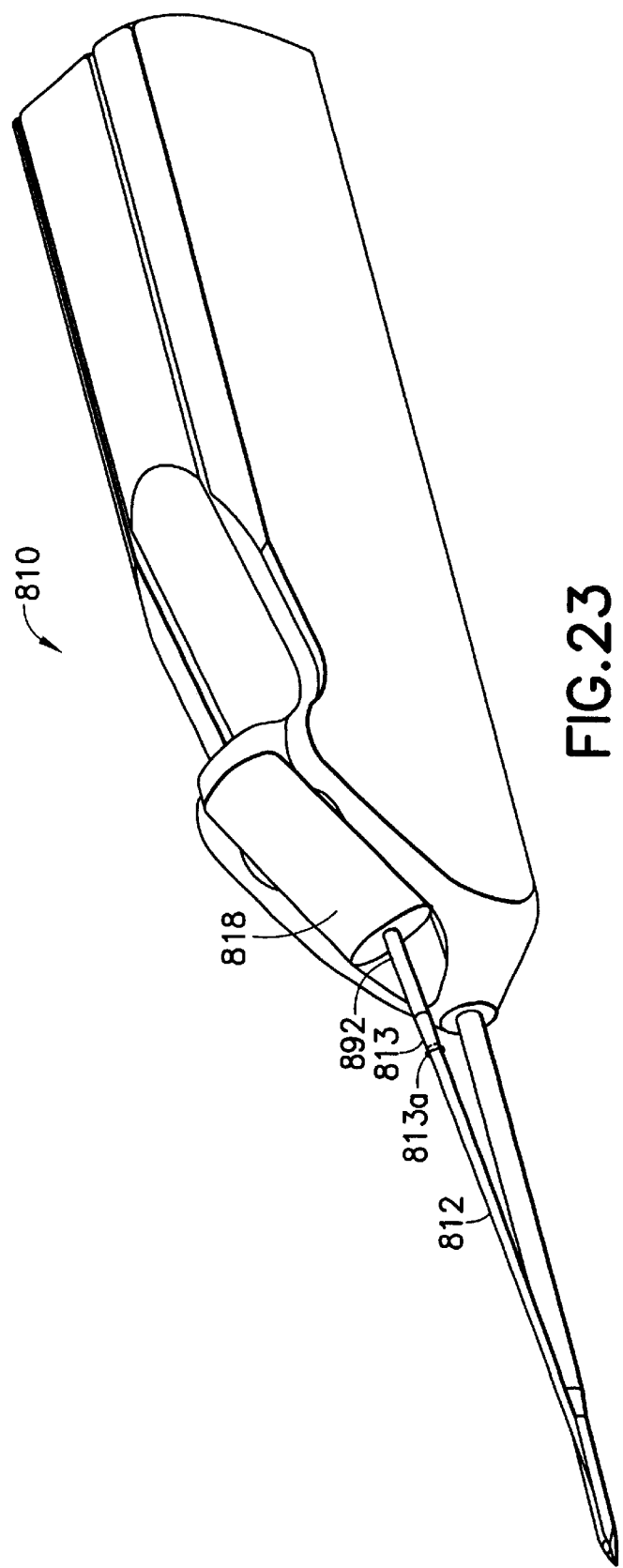
FIG. 23 is a perspective view of a fifth embodiment of fracture fixation system.

Referring now to FIG. 23, the pin handle 818 of the fixation system 810 may be provided with a set of fixation pins, substantially as described above with respect to the first embodiment but having a variety of distal dimensions. For example, it may be desirable to insert a pin 812 into a phalangeal medullary canal having a relatively smaller distal diameter than would be desirable for a metacarpal bone. However, in order to permit the pin handle 818 to easily accommodate and stably hold pins having a variety of distal dimensions, the dimensions of the proximal portion 892 of the pins may be provided with a preferably uniform dimension. As such, some fixation pins 812 may have a distally tapered portion 813 (or alternatively a step 813a, shown in dotted line), along the proximal portion 892 of the pin to taper to their respective distal dimension.

Turning now to FIG. 24, a fixation system may be provided with a plurality, or set 900, of fixation pins 912a, 912b, 912c, having the same or different relative sizes. Each individual pin is smaller than the medullary canal of the bone, yet when implanted in combination with one or more others of the set provides a fixation system which approximates the inner diameter of the medullary canal in order to provide the required fixation. Referring to FIG. 25, the pins are individually inserted into the medullary canal of the fractured bone substantially as described above; i.e., using an instrument including a shaft having a guiding groove and provided with a shaft handle for manipulating the shaft, and a pin handle coupled to the proximal end of the pin. A first pin 912a is provided in the pin handle and inserted into the medullary canal 913 of a bone 915 to extend across a fracture 911 in the bone, as described above. A second pin 912b is inserted alongside the first pin 912a, and optionally additional pins, e.g., 912c, are likewise inserted. The distal ends of the pins may diverge to rest or imbed in different portions of the bone, as shown or, alternatively, may remain substantially aligned. Referring to FIGS. 25 and 26, a cylindrical collet 917 is then positioned over the exposed proximal ends of the pins to constrain the pins together such that the pins are substantially prevented from relative axial rotation. The collet 917 preferably includes a central opening 919 adapted to stably secure the pins. For example, for three pins, the central opening 919 may be circular with a diameter adapted to hold the three pins together. In addition, the collet 917 also preferably includes a means for securing the collet, and therefore the proximal ends of the fixation pins, to the fractured bone, e.g., external and preferably self-tapping threads 921. An external flange 923 adapted to assist in seating the collet at the desired depth in the bone is also preferably provided. As such, the fixation system provides torsional stabilization to the fracture.

Turning now to FIGS. 27 and 28, in another torsionally stabilized fracture fixation system, two pins 1012a, 1012b are inserted into the bone 1015 to bridge the fracture 1011 as described above. A collet 1017 having three openings 1019a, 1019b, 1019c (or a collet 1117 having a single clover-shaped opening 1119, as shown in FIG. 29) is provided over the proximal ends of the pins with the pins extending through two of the openings 1019a, 1019b. In the remaining opening 1019c, a nail 1121 is provided and secured into the bone to immobilize the collet 1017 relative to the bone.

There have been described and illustrated herein several embodiments of a fracture fixation system. While particular embodiments of the invention have been described, it is not intended that the invention be limited thereto, as it is intended that the invention be as broad in scope as the art will allow and that the specification be read likewise. Thus, while some embodiments of the fixation system have been particularly disclosed for the fixation of fractured metacarpal bones, it will be appreciated that the system may be used to fixate bones of similar or smaller size and for which similar problems exist with respect to fracture fixation, e.g., metatarsal bones in the foot and the phalanges of the fingers and toes. In addition, pediatric arm bones, e.g., ulna and radial bones, can be similarly treated. Therefore, the teaching here is for the use of the system of the invention with the like bones. In addition, while particular materials have been disclosed with respect to the various components of the system of the invention, it will be appreciated that other suitable materials may be used as well. For example, while a metal fixation pin has been described, less preferred alternative materials for the fixation pin are nonmetals, in particular, bioabsorbable materials. Furthermore, while particular dimensions and angles have been disclosed and provide superior results, it will be understood that the components may be sized to other suitable dimensions and angles, as long as they are adapted to be used in a system to immobilize metacarpal bones and the like. For example, while the distal portion of the fixation pin and the distal surface of the groove are both preferable angled at between 5°–8°, it will be appreciated that other suitable angles, e.g., between 3° and 15°, may also be used. Also, while indentations are disclosed as finger gripping means, other finger gripping means, e.g., knurls, ridges, grooves, and nubs, may additionally or alternatively be used. In addition, while the bone boring shaft component is described as a drill in the first embodiment, it will be appreciated that the shaft component is not required to have any cutting edges, and may be provided with a sharp point to enter the bone. Furthermore, while machined handles are disclosed for moving the fixation pin relative to the shaft component, it will be appreciated that pliers or the like may similarly be used to hold and move the pin through the guiding means of the shaft. Further yet, while pins have been described for holding the drill shaft in the main handle, it will be appreciated that other means for fixing the drill in the handle. In addition, while a cylindrical collet has been shown holding the proximal ends of pins together, it will be appreciated that devices having different shapes and configurations can likewise be used to constrain the pin ends together. For example, sleeves, bands, clips, staples, etc., may be used. Also, while in one embodiment a nail is shown extending through the collet, it will be appreciated that a screw or similar fastener can likewise be used. It will therefore be appreciated by those skilled in the art that yet other modifications could be made to the provided invention without deviating from its spirit and scope as so claimed.

What is claimed is:

1. A fracture fixation system for stabilizing a fracture of a bone, said system comprising:

a) a plurality of fixation pins each having a proximal end and a distal end, said fixation pins each being sized to fit together within the medullary canal of the bone and having a combined stiffness sufficient to immobilize the fracture and an individual flexibility sufficient to permit each of said plurality of fixation pins to bend to facilitate insertion into the medullary canal; and b) an elongate shaft having a proximal end, a distal end with means for boring a hole in the bone, and a means adjacent said distal end of said shaft for guiding each said fixation pin into the medullary canal, said fixation pins and said shaft are both adapted such that said distal end of each of said fixation pins is movable beyond said distal end of said shaft.

2. A fracture fixation system according to claim 1, further comprising:

c) a first handle means coupled to said proximal end of one of said fixation pins for facilitating movement of said one of said fixation pins relative to said shaft and through said pin guide.

3. A fracture fixation system according to claim 2, wherein:

said first handle means includes a finger engageable structure which facilitates movement of said one of said fixation pins into the medullary canal.

4. A fracture fixation system according to claim 1, wherein:

said pin guide is a groove in said shaft at or adjacent said distal end of said shaft.

5. A fracture fixation system according to claim 4, wherein:

said groove includes a proximal sloped surface and distal curved surface.

6. A fracture fixation system according to claim 1, wherein:

said means for boring includes a plurality of cutting edges which meet at a point.

7. A fracture fixation system according to claim 1, wherein:

said plurality of fixation pins includes at least one fixation pin having a first distal diameter and at least one fixation pin having a second distal diameter different than said first distal diameter.

8. A fracture fixation system according to claim 7, wherein:

each of said plurality of fixation pins is provided with a distal diameter between approximately 0.035 inch–0.060 inch.

9. A fracture fixation system according to claim 1, wherein:

at least one of said pins includes a proximal portion having a first diameter and a distal portion having a second diameter smaller than said first diameter.

10. A fracture fixation system according to claim 1, further comprising:

c) a means for securing said proximal ends of said fixation pins together.

11. A fracture fixation system according to claim 10, wherein:

said means for securing additionally secures said fixation pins to the bone.

12. A fracture fixation system according to claim 11, wherein:

said means for securing includes a collet surrounding said proximal ends of said fixation pins, and a fastener extending through said collet and into the bone.

13. A fracture fixation system according to claim 1, further comprising:

c) a means for securing said proximal ends of said fixation pins to said bone.

14. A fracture fixation system according to claim 13, wherein:

said means for securing is provided with self-tapping threads which engage the bone.

15. A fracture fixation system according to claim 1, wherein:

said fixation pins are sized to fit together within the medullary canal of one of a human metacarpal bone, human metatarsal bone, human phalangeal bone, pediatric ulna bone, and pediatric radial bone.

16. A fracture fixation system for stabilizing a fracture, said system comprising:

a) a fixation pin having a proximal portion and a distal portion and being sized to fit within a medullary canal of the bone, said proximal portion having a first diameter, and said distal portion having a non-linear shape and a second diameter smaller than said first diameter; and b) an elongate shaft having a proximal portion, a distal portion with a boring tip, a longitudinal axis, and a pin guide in said distal portion, said pin guide defining a non-linear shape substantially similar to said non-linear shape of said distal portion of said fixation pin, such that when said boring tip of said shaft is entered into the bone and said fixation pin is moved distally relative to said shaft, said pin guide guides said fixation pin into said medullary canal of the bone at an angle relative to said longitudinal axis.

17. A fracture fixation system according to claim 16, wherein:
said pin includes one of a taper and a step between said first diameter and said second diameter.

18. A fracture fixation system according to claim 16, wherein:
said non-linear shape of said distal portion of said fixation pin includes a proximal straight first portion and a curved distal second portion.

19. A fracture fixation system according to claim 16, wherein:
said fixation pin is sized to fit into the medullary canal of one of a human metacarpal bone, human metatarsal bone, human phalangeal bone, pediatric ulna bone, and pediatric radial bone.

* * * * *